(12) United States Patent
Siegwart et al.

(10) Patent No.: US 6,747,183 B2
(45) Date of Patent: Jun. 8, 2004

(54) ADHESIVE BANDAGE WITH IMPROVED COMFORT AND FIT

(75) Inventors: Kathleen Siegwart, Milford, NJ (US); Jennifer Mueller, Hillsborough, NJ (US); Vincent Petersack, Eastampton, NJ (US)

(73) Assignee: Johnson & Johnson Consumer Products, Inc., Skillman, NJ (US)

( * ) Notice: Subject to any disclaimer, the term of this patent is extended or adjusted under 35 U.S.C. 154(b) by 86 days.

(21) Appl. No.: 09/954,912

(22) Filed: Sep. 18, 2001

(65) Prior Publication Data

US 2003/0055369 A1 Mar. 20, 2003

(51) Int. Cl.$^7$ .................................................. A61F 5/00
(52) U.S. Cl. .......................................... 602/58; 602/43
(58) Field of Search ............................... 602/41–59, 900

(56) References Cited

U.S. PATENT DOCUMENTS

D238,007 S  * 12/1975  Gernei ........................ 72/356
6,191,338 B1 * 2/2001  Haller ......................... 602/55

* cited by examiner

*Primary Examiner*—Weilun Lo
*Assistant Examiner*—Linh Truong

(57) ABSTRACT

An adhesive bandage having a backing material; an adhesive applied to at least one second major surface of the backing material; and a wound contacting pad secured to the backing by a portion of said adhesive. The bandage has a tapered portion and a non-tapered portion. The length of the tapered portion of the bandage ranges from about 30% to about 70% of the total length of the bandage.

7 Claims, 4 Drawing Sheets

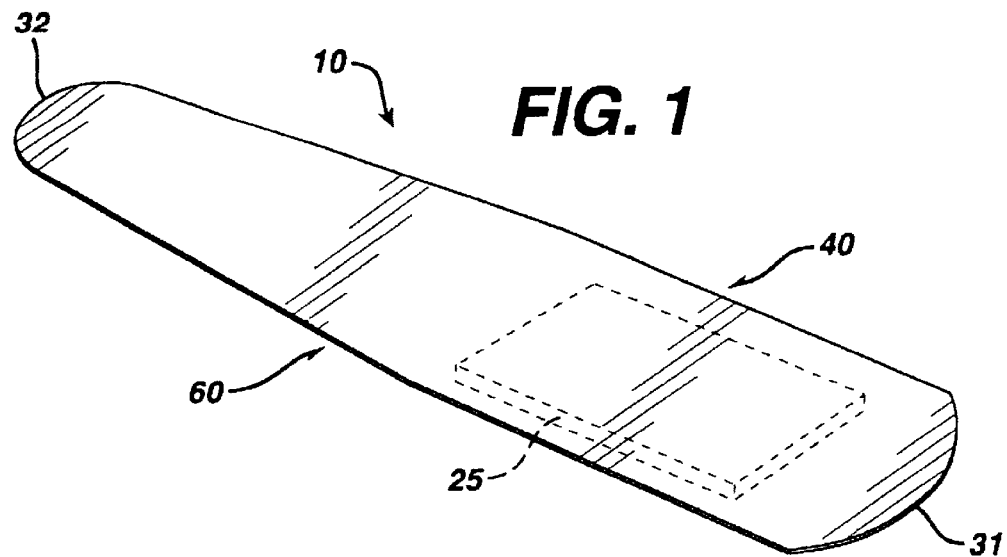
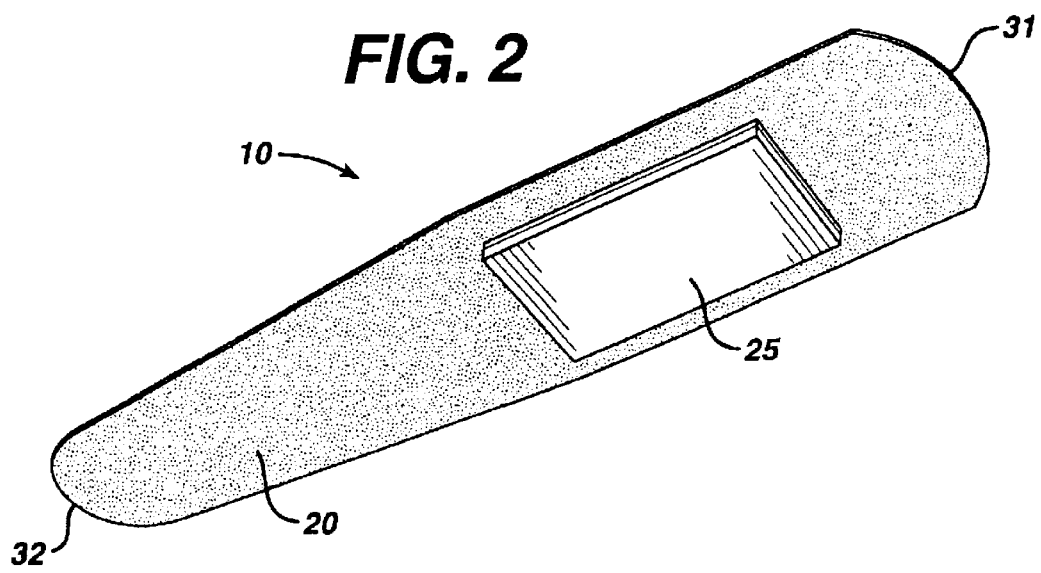

PRIOR ART BANDAGE

ADHESIVE BANDAGE WITH IMPROVED COMFORT AND FIT

BACKGROUND OF THE INVENTION

1. Field of the Invention

This invention relates to an adhesive bandage having improved comfort and fit during use by the consumer. The adhesive bandage has a backing material, an adhesive, and a wound-contacting pad. The adhesive bandage is designed to be more comfortable when worn over wounds in areas that bend, e.g., finger joints. The bandage is tapered at one side thereof to provide the improved comfort.

2. Description of the Prior Art

Adhesives bandages are widely used to cover and protect wounds on various parts of the human body. A variety of adhesive bandage structures and designs are commercially available to attend to different patient needs, based on the location and severity of the wound.

It is known that fingers are one of the most frequently injured regions of the body. The bandages frequently applied to wounds on fingers have a rectangular shape or rounded corners created by the removal of some material from the corners of the rectangle. These bandages typically have 3% or less of the total original rectangular area removed. The use of these bandages may present some discomfort as well as poor skin adhesion during use. The discomfort and poor adhesion may be due at least in part to the shape of the bandage. There is a need for a finger bandage that provides improved comfort.

In a co-pending Japanese Patent Application No. 332101/99, a bandage having tapered ends with slits on either side of the absorbent pad was disclosed. The slits were believed to be necessary to reduce stress in the area of the bandage surrounding the absorbent pad. Although the bandage provides improved comfort, the bandage is difficult to make on a commercial scale due to the slits provided therein. Despite the disclosure of the prior art, there is a continuing need for a finger bandage that provides improved comfort during use.

SUMMARY OF THE INVENTION

The present invention provides an adhesive bandage having:

- a backing material having a first major surface and a second major surface;
- an adhesive applied to at least one of said first and second major surfaces; and a wound contacting pad secured to said backing material by a portion of said adhesive;
- said bandage having a longitudinal axis, a transverse axis substantially perpendicular to said longitudinal axis, and a perimeter;
- the perimeter of said bandage comprising an upper edge, a lower edge, a first rounded side edge and a second rounded side edge;
- said upper edge comprising a first linear segment and a second linear segment joined at a point of inflection and having a first free end and a second free end;
- said lower edge comprising a first linear segment and a second linear segment joined at a point of inflection and having a first free end and a second free end;
- the first free end of said upper edge being joined to one end of said first rounded side edge and the first free end of said lower edge being joined to the other end of said first rounded side edge;
- the second free end of said upper edge being joined to one end of said second rounded side edge and the second free end of said lower edge being joined to the other end of said second rounded side edge;
- the radius of curvature of said first rounded side edge being greater than the radius of curvature of said second rounded side edge.

BRIEF DESCRIPTION OF THE DRAWINGS

The present invention will be more clearly understood by reference to the accompanying drawings in which:

FIG. 1 is a front perspective of one embodiment of an adhesive bandage in accordance with the present invention;

FIG. 2 is a rear perspective of the adhesive bandage of FIG. 1;

DETAILED DESCRIPTION OF PREFERRED EMBODIMENTS

Figure 3:
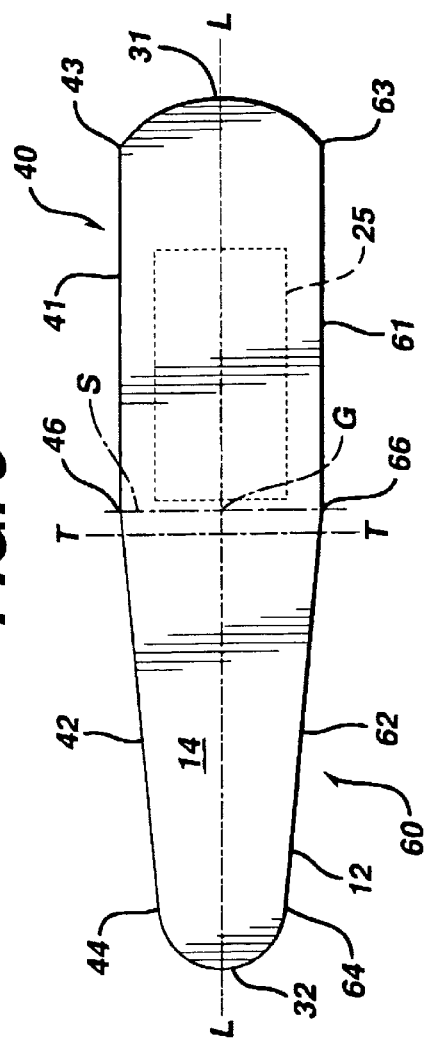
FIG. 3 is a top plan view of the adhesive bandage of FIG. 1.

The bandage of the present invention comprises a backing material. Any conventional backing material may be utilized. Suitable backing materials include, but are not limited to, polyurethane films; polyolefin films, such as polyethylene and polypropylene films; polyvinylchloride films; ethylene vinyl acetate films; woven fabrics; nonwoven fabrics; and the like. Backings may be perforated or nonperforated.

A woven backing material useful in the practice of the present invention has a polyester fiber, such as polyethylene terephthalate or polybutylene terephthalate, in the warp direction and a polyamide fiber, such as nylon 6 or nylon 6,6 in the fill direction. Alternatively, the woven backing material may a have polyethylene terephthalate fiber, in the warp direction and a polybutylene terephthalate fiber in the fill direction. Such backings are known and are used commercially.

An adhesive is applied to at least one of the first and second major surfaces of the backing material. A portion of the adhesive is used to secure a wound-contacting pad to the backing material, the remainder of the adhesive functioning during use to hold the bandage on the skin of the user. The adhesives may be hot melt adhesives. Examples of suitable adhesives include, but are not limited, to those based on styrenic block copolymers and tackifying resins such as HL-1491 from HB-Fuller Co. (St. Paul Minn.), H-2543 from ATO-Findley (Wawatausa, Wis.), and 34-5534 from National Starch & Chemical (Bridgewater, N.J.). Ethylene copolymers, including ethylene vinyl acetate copolymers, may also be used as adhesives in the practice of the present invention.

Suitable adhesives also include acrylic based, dextrin based, and urethane based adhesives as well as those based on natural and synthetic elastomers. The adhesives may also include amorphous polyolefins including amorphous polypropylene, such as HL-1308 from HB Fuller or Rextac RT 2373 from Huntsman (Odesssa, Tex.). The adhesive may be based on synthetic elastomers or natural rubber modified, where necessary or desirable, with tackifiers and antioxidants as known in the art.

The adhesive can be applied to the backing material, e.g., by spraying, slot die coating or other methods well-known for this purpose. The adhesive can be applied by control coating, control weaving, control fiberization, meltblowing, flexo coating, screen printing, or other discontinuous coating methods. The amount of adhesive typically applied is well known in the art; however, the coating weight will typically range from about 20 grams per square meter ("gsm") to about 100 gsm.

A wound-contacting pad is secured to the backing by a portion of the adhesive in order to cushion the wound and protect the wound from contamination by dirt. The wound-contacting pad may be placed in the center of the backing. Alternatively, as is the case in one preferred embodiment, the wound-contacting pad may be offset from the center of the backing. For example, the wound contacting pad may be placed with one end closer to one rounded side edge than the other rounded side edge. Preferably, the wound-contacting pad is located closer to the first rounded side edge, i.e., the rounded side edge which has the greater radius of curvature. Typically, one end of the wound-contacting pad is placed from about 10 mm to about 15 mm from the first rounded side edge. Preferably, one end of the wound-contacting pad is placed from about 11 mm to about 14 mm from the first rounded side edge.

As is known in the art, the width of the wound-contacting pad may be more or less equal to the width of the backing. Alternatively, the width of the wound-contacting pad may be significantly less than the width of the backing material to thereby provide a bandage having what is known as an "island pad" configuration. The wound-contacting pad comprises a fibrous layer which may be made from various fibers including rayon fibers; natural fibers, such as, but not limited to, cotton and wood pulp; synthetic fibers, such as, but not limited to, polyester, polyamide, and polyolefin fibers; copolymer fibers; and combinations thereof. The fibers may be bicomponent fibers. For example, the fibers may have a core of one polymer, and a sheath of a different polymer. Typically, the fibers constituting the wound-contacting pad have deniers ranging from about 1 to about 9, although other deniers are useful as well.

The fibers comprising the fibrous layer of the wound-contacting pad may, if desired, be bonded, e.g., by the application of a suitable adhesive. Alternatively, where the fibrous layer includes thermoplastic fibers, the fibrous layer may be bonded by heat treatment as is known in the art. In addition, the upper surface of the fibrous layer may be covered by a porous net-like material made from a polyolefin such as polyethylene, polypropylene or ethylene-vinyl acetate copolymer. Such materials are known in the art and are commercially available under the tradename DELNET. The basis weight of the wound-contacting pad (i.e., the fibrous layer covered with the porous netting) is not particularly limited, but typically ranges from 0.003 g/cm$^2$ to 0.015 g/cm$^2$. The size of the wound-contacting pad will vary depending on the wound to be protected or treated.

The bandage of the present invention has a length, l, in its longitudinal direction, and a maximum width, $W_{max}$, in its transverse direction. The width of the bandage at its widest point typically ranges from about 10 mm to about 30 mm. The length of the bandage typically ranges from about 60 mm to about 90 mm, preferably from about 70 mm to about 80 mm. As will be seen hereinafter, the bandage of the present invention has a tapered portion and a non-tapered portion. The tapered portion of the bandage has a length which ranges from about thirty percent (30%) to about seventy percent (70%) of the total length, l, of the bandage. Preferably, the tapered portion of the bandage has a length which ranges from about thirty-five percent (35%) to about sixty-five percent (65%) of the total length of the bandage.

For acceptable adhesion of the bandage to the skin and protection of the wound, the length of the wound contacting pad is typically from about 20 percent to about 70 percent, preferably from about 25 percent to about 50 percent of the length of the backing material.

Examples are set forth below to further illustrate the nature of the invention and the manner of carrying it out. However, the invention should not be considered as being limited to the details thereof.

Figure 4:
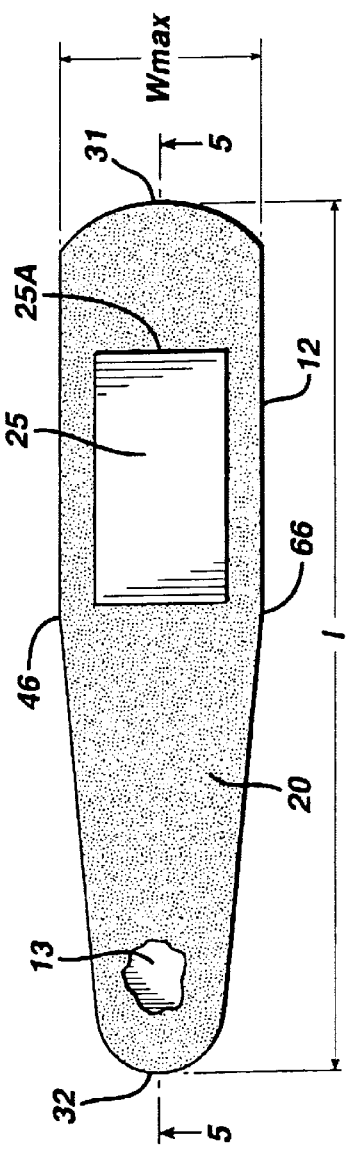
FIG. 4 is a bottom plan view of the adhesive bandage of FIG. 1.

Referring now to the appended drawings, bandage 10 comprises a backing material 12, an adhesive 20 (shown in stippling in FIGS. 2 and 4), and a wound-contacting pad 25. As shown in FIG. 3, bandage 10 has a longitudinal axis, L—L, and a transverse axis, T—T. The longitudinal axis and the transverse axis intersect each other at an angle of substantially 90°. The bandage has an upper edge 40 on one side of the longitudinal axis, a lower edge 60 on the other side of the longitudinal axis, a first rounded side edge 31 and a second rounded side edge 32. The backing material has a first major surface 13 and a second major surface 14. The adhesive 20 is applied to the first major surface 13 of the backing material 12. The wound-contacting pad 25 is secured to the backing material 12 by a portion of the adhesive 20.

The upper edge 40 of the bandage has a first linear segment 41, a second linear segment 42, a first free end 43, and a second free end 44, the first linear segment 41 being joined to the second linear segment 42 at a point of inflection 46.

The lower edge 60 of the bandage has a first linear segment 61, a second linear segment 62, a first free end 63, and a second free end 64, the first linear segment 61 being joined to the second linear segment 62 at a point of inflection 66.

The length of the first linear segment 41 of the upper edge 40 and the length of the first linear segment 61 of the lower edge 60 may range from about 30 mm to about 55 mm, preferably from about 35 mm to about 45 mm. The length of the second linear segment 42 of the upper edge 40 and the length of the second linear segment 62 of the lower edge 60 may range from about 20 mm to about 45 mm, preferably from about 25 mm to about 35 mm.

The first free end 43 of the upper edge 40 is joined to one end of the first rounded side edge 31 and the first free end 63 of the lower edge 60 is joined to the other end of the first rounded side edge 31.

The second free end 44 of the upper edge 40 is joined to one end of the second rounded side edge 32 and the second free end 64 of the lower edge 60 is joined to the other end of the second rounded side edge 32.

The first rounded side edge 31 has a radius of curvature which is greater than the radius of curvature of the second rounded side edge 32. The radius of curvature of the first rounded side edge 31 ranges from about 0.3 inch to about 0.75 inch. The radius of curvature of the second rounded side edge 32 ranges from about 0.15 inch to about 0.40 inch. In a specific embodiment, first rounded side edge 31 has a radius of curvature of 0.5 inch and second rounded side edge 32 has a radius of curvature of 0.25 inch.

As mentioned earlier herein, the adhesive bandage of the present invention comprises a tapered portion and a non-tapered portion. Referring to FIG. 3, the length of the tapered portion of the bandage is the distance measured along the longitudinal axis, L—L, from the tip of second rounded side edge 32 to the point G where the longitudinal axis, L—L, intersects a line S joining inflection points 46 and 66. Still referring to FIG. 3, the length of the non-tapered portion of the bandage is the distance measured along the longitudinal axis, L—L, from the tip of first rounded side edge 31 to the aforementioned point G. The sum of the lengths of the tapered portion and non-tapered portion of the bandage equals the total length, 1, of the bandage.

EXAMPLES

Finite elemental analysis was performed on the inventive adhesive bandage shown in FIGS. 1–5 and a non-tapered adhesive bandage to determine regions of the bandage that are stressed during use. It is believed that these stressed regions result in discomfort and poor adhesion of the bandage when in use. The study simulates the tension encountered by an adhesive bandage which, after application to a joint such as a finger, a knee, or an elbow, is flexed. In this simulation, the product is applied on a substratum with elastic characteristics similar to human skin. The substratum is then elongated in the longitudinal and transverse directions thus exposing the product to stress.

Figure 5:
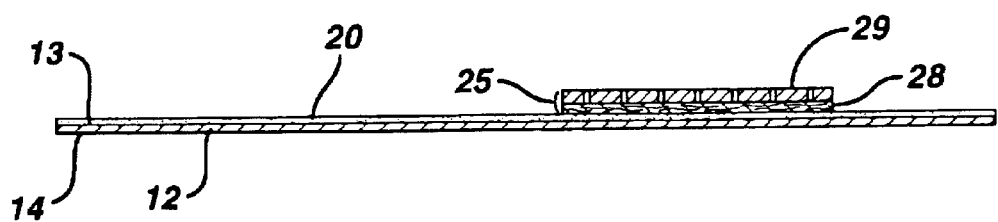
FIG. 5 is a longitudinal sectional view taken along line 5—5 of FIG. 4.

The inventive bandage presented for finite elemental analysis was bandage 10 shown generally in FIGS. 1–5 with the wound-contacting pad 25 thereof consisting of a fibrous layer 28 covered by a porous plastic netting 29 (see FIG. 5). This bandage had a length of about 76 mm and a maximum width of about 19 mm. The length of its tapered portion was about 40 mm and the length of its non-tapered portion was about 36 mm. The radius of curvature of first rounded side edge 31 was about 0.5 inch; the radius of curvature of second rounded side edge 32 was about 0.25 inch. Wound-contacting pad 25 had a length of about 22 mm and a width of about 11.7 mm. The distance between side edge 25a of wound-contacting pad 25 and the tip of rounded side edge 31 was about 13 mm.

Figure 6:
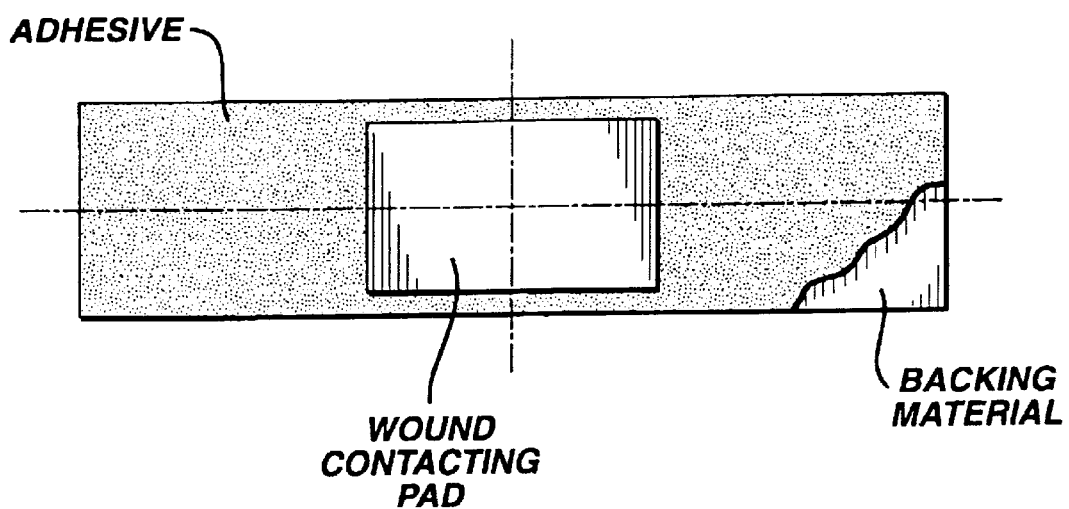
FIG. 6 is a bottom plan view showing a typical, commercially available non-tapered adhesive bandage.

The prior art bandage shown generally in FIG. 6 is a typical, commercially available rectangular (no tapered portions) adhesive bandage 19 mm wide and 76 mm long. The wound-contacting pad has the same fibrous layer 28 and porous netting cover 29 as that descirbed earlier herein for wound-contacting pad 25 of bandage 10. The wound-contacting pad of the prior art bandage was about 14 mm wide and about 25 mm long and was located midway between the two ends and two sides of the bandage as shown in FIG. 6.

For finite elemental analysis, the bandage of FIGS. 1–5 and the prior art bandage of FIG. 6 were represented as being perfectly bonded to a 1 mm substrate simulating skin. The following modulus of elasticity coefficients were utilized: substrate: 1.75 MPa; bandage backing: 12.4 MPa; fibrous layer of wound-contacting pad: 1.4 Mpa; and porous netting covering of wound-contacting pad: 1 MPa. The two bandage models were discretized into meshes of quadratic solid elements with 20 nodes and 3 displacement degrees of freedom per node. The number of finite elements utilized was 4,831 for the inventive bandage and 4873 for the prior art bandage.

In the analysis, the two bandage models were stressed with 8 mm displacement force in the transverse direction and 12 mm displacement force in the longitudinal direction. A nonlinear iterative analysis with finite deformations was performed on each of the bandages. The tension in the tranverse and longitudinal directions for ¼ of each adhesive bandage was measured using finite elemental analysis, and the Von Mises stress was calculated. The results are shown in Table 1 as the percent of area of the bandage with high stress (greater than 3.5 N/mm$^2$).

TABLE 1

| Bandage of | % Area With High Stress |
| --- | --- |
| FIG. 1–5 | 15 |
| FIG. 6 | 50 |

The bandage of FIG. 6 had a greater area of stress than the inventive bandage of FIGS. 1–5. The data shows that the adhesive bandages of the present invention provide a more comfortable, better fitting bandage.

We claim:

1. An adhesive bandage comprising:
   a backing material having a first major surface and a second major surface;
   an adhesive applied to at least one of said first and second major surfaces; and a wound contacting pad secured to said backing material by a portion of said adhesive;
   said bandage having a longitudinal axis, a transverse axis substantially perpendicular to said longitudinal axis, and a perimeter;
   the perimeter of said bandage comprising an upper edge, a lower edge, a first rounded side edge and a second rounded side edge;
   said upper edge comprising a first linear segment and a second linear segment joined at a point of inflection and having a first free end and a second free end;
   said lower edge comprising a first linear segment and a second linear segment joined at a point of inflection and having a first free end and a second free end;
   the first free end of said upper edge being joined to one end of said first rounded side edge and the first free end of said lower edge being joined to the other end of said first rounded side edge;
   the second free end of said upper edge being joined to one end of said second rounded side edge and the second free end of said lower edge being joined to the other end of said second rounded side edge;
   the radius of curvature of said first rounded side edge being greater than the radius of curvature of said second rounded side edge,
   said bandage having a tapered portion and a non-tapered portion, the length of said tapered portion ranging from about 30% to about 70% of the total length of the bandage.

2. The adhesive bandage of claim 1 wherein the length of said tapered portion ranges from about 35% to about 65% of the total length of the bandage.

3. The adhesive bandage of claim 1 wherein the radius of curvature of said first rounded side edge ranges from about 0.3 inch to about 0.75 inch.

4. The adhesive bandage of claim 1 wherein the radius of curvature of said first rounded side edge is about 0.50 inch.

5. The adhesive bandage of claim 1 wherein the radius of curvature of said second rounded side edge ranges from about 0.15 inch to about 0.4 inch.

6. The adhesive bandage of claim 1 wherein the radius of curvature of said second rounded side edge is about 0.25 inch.

7. The adhesive bandage of claim 1 wherein the radius of curvature of said first rounded side edge is about 0.5 inch and the radius of curvature of said second rounded side edge is about 0.25 inch.

* * * * *